(12) United States Patent
Rarama (10) Patent No.: US 9,897,591 B2
(45) Date of Patent: Feb. 20, 2018

(54) BREATH ALCOHOL IGNITION INTERLOCK SYSTEM

(71) Applicant: Alcohol Countermeasure Systems (International) Inc., Toronto, CA (US)

(72) Inventor: Exequiel Rarama, Brampton (CA)

(73) Assignee: Alcohol Countermeasure Systems (International) Inc., Toronto, Ontario (CA)

( * ) Notice: Subject to any disclaimer, the term of this patent is extended or adjusted under 35 U.S.C. 154(b) by 74 days.

(21) Appl. No.: 15/028,275

(22) PCT Filed: Sep. 21, 2015

(86) PCT No.: PCT/CA2015/050925
§ 371 (c)(1),
(2) Date: Apr. 8, 2016

(87) PCT Pub. No.: WO2016/044926
PCT Pub. Date: Mar. 31, 2016

(65) Prior Publication Data
US 2016/0252492 A1 Sep. 1, 2016

Related U.S. Application Data

(60) Provisional application No. 62/053,866, filed on Sep. 23, 2014.

(51) Int. Cl.
*G06K 9/00* (2006.01)
*G01N 33/497* (2006.01)
*B60K 28/02* (2006.01)
*B60K 28/06* (2006.01)
*G05B 1/01* (2006.01)
(Continued)

(52) U.S. Cl.
CPC ......... *G01N 33/4972* (2013.01); *B60K 28/02* (2013.01); *B60K 28/06* (2013.01); *G05B 1/01* (2013.01); *G06K 9/00248* (2013.01); *G06K 9/209* (2013.01); *G06K 9/2027* (2013.01); *G06K 9/22* (2013.01); *G06K 9/4661* (2013.01); *B60W 2540/24* (2013.01)

(58) Field of Classification Search
CPC ........... G06K 9/00; G01N 33/00; B60K 28/00
USPC ............. 382/103; 73/23.3; 701/45; 600/531, 600/532, 534, 538, 539, 543
See application file for complete search history.

(56) References Cited

U.S. PATENT DOCUMENTS

| | | | |
|---|---|---|---|
| 8,359,901 B2 * | 1/2013 | Freund | G07C 5/0891 73/23.3 |
| 8,795,187 B2 * | 8/2014 | Morley | B60K 28/063 180/272 |
| 2013/0338880 A1 | 12/2013 | Connerty et al. | |

* cited by examiner

*Primary Examiner* — Abolfazl Tabatabai
(74) *Attorney, Agent, or Firm* — Head, Johnson, Kachigian & Wilkinson, PC (57) ABSTRACT

The system is of the type for use by a person and including a handpiece and an imaging device, the handpiece containing a breath alcohol tester and the imaging device being adapted to capture an image including the handpiece when a breath sample is delivered to the handpiece. The improvement includes a sensor arrangement and a computing functionality. The sensor arrangement is adapted to provide information from which an orientation and position of the handpiece can be calculated. The computing functionality is adapted to: generate a calculated orientation and position of the handpiece; and if a face appears in the image, precisely locate the features thereof. The features of the face are located using the calculated orientation and position of the handpiece.

14 Claims, 10 Drawing Sheets

(51) Int. Cl.
*G06K 9/20* (2006.01)
*G06K 9/22* (2006.01)
*G06K 9/46* (2006.01)
*G01N 1/22* (2006.01)

BREATH ALCOHOL IGNITION INTERLOCK SYSTEM

FIELD OF THE INVENTION

The invention relates to the field of breath alcohol ignition interlock devices.

BACKGROUND OF THE INVENTION

In many jurisdictions, persons that have been convicted of driving under the influence of alcohol are extended driving privileges on a restricted basis for a period of time following conviction. A common restriction involves the mandatory inclusion of a breath alcohol ignition interlock device [BAIID] in each vehicle operated by the offender. In order to operate the vehicle, an operator must deliver suitable breath samples to the device periodically, and also at initial start-up; in this context, "suitable" means, inter alia, containing alcohol below a predetermined threshold. In the event that the operator delivers samples that contain alcohol above the threshold [a "fair"], the driving privileges of the offender may be withdrawn altogether and incarceration may result.

Because of the serious consequences associated with a fail, it is known for imaging or biometric technology to be deployed in conjunction with the BAAID, so that the responsible public authority can be confident that the person delivering the unsuitable breath sample is the person punished.

Similarly, because of the serious consequences associated with a fail, it is known for offenders to attempt to "spoof" the BAIID in various ways. For example, it is known for an offender to obtain a "dummy" handset, and to deliver a breath sample into the dummy handset while a third party, out of view of the imaging device, delivers a clean sample into the actual handset.

SUMMARY OF THE INVENTION

Forming one aspect of the invention is an improved breath alcohol ignition interlock system of the type for use by a person and including a handpiece and an imaging device. The handpiece contains a breath alcohol tester and the imaging device is adapted to capture an image including the handpiece when a breath sample is delivered to the handpiece. The improvement comprises a sensor arrangement and a computing functionality. The sensor arrangement is adapted to provide information from which an orientation and position of the handpiece can be calculated. The computing functionality is adapted to: generate a calculated orientation and position of the handpiece; and if a face appears in the image, precisely locate the features thereof. The features of the face are located using the calculated orientation and position of the handpiece.

According to another aspect of the invention, the features of the face can be further located using stored data associated with facial geometry.

According to another aspect of the invention, the features of the face can be further located using stored data associated with the geometry of the face of the person.

According to another aspect of the invention, if the handpiece appears in the image, the device can precisely identify the location and orientation of the handpiece, using stored data associated with the geometry of the handpiece.

According to another aspect of the invention, the features of the face can be located using the location and orientation of the handpiece as identified.

According to another aspect of the invention, the sensor arrangement can comprise an accelerometer and a gyroscope disposed interiorly of the handpiece.

According to another aspect of the invention, the handpiece can include a light which is selectively triggered by the system according to a pattern and can be perceived by the imaging device; and the imaging device can sense the light and compare the perceived light against the pattern for anti-circumvention purposes.

Other advantages and features of the advantage will become apparent upon review of the following detailed description and the appended drawings, the latter being described briefly hereinafter.

DETAILED DESCRIPTION OF THE EXEMPLARY EMBODIMENT

Reference is now made to the Figures.

Figure 1:
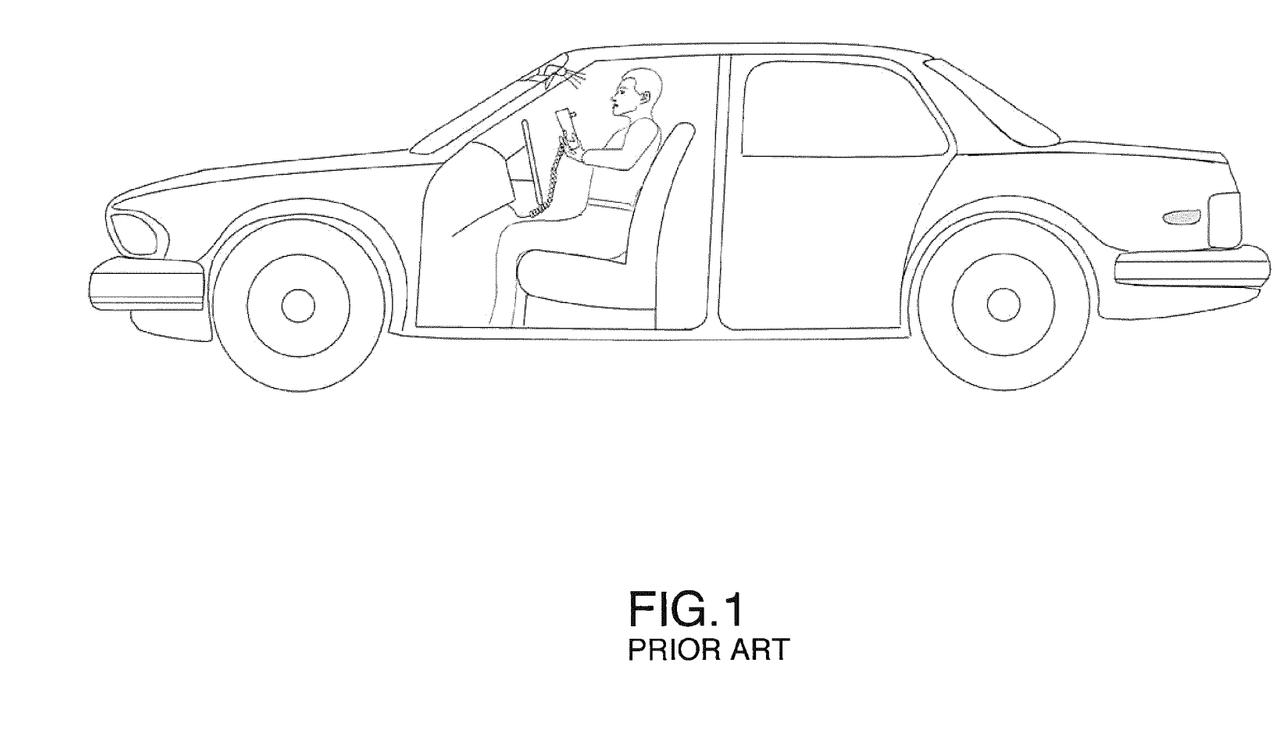
FIG. 1 is a side schematic view of a prior art breath alcohol interlock system in a vehicle.

As an initial matter, the exemplary system will be understood to be of the general type that is shown in FIG. 1. This system, which is for use by a person, includes a handpiece and an imaging device. The handpiece contains a breath alcohol tester. The imaging device is adapted to capture an image including the handpiece when a breath sample is collected, for the purpose of the identification of the contributor of the sample. In the system shown in FIG. 1, the imaging device is an infrared camera mounted in the roof of a vehicle, infrared functionality being of advantage in that it does not demand supplemental lighting in conditions of darkness. Breath alcohol testers and infrared imaging devices are well known and according further detail is neither required nor provided.

Figure 2:
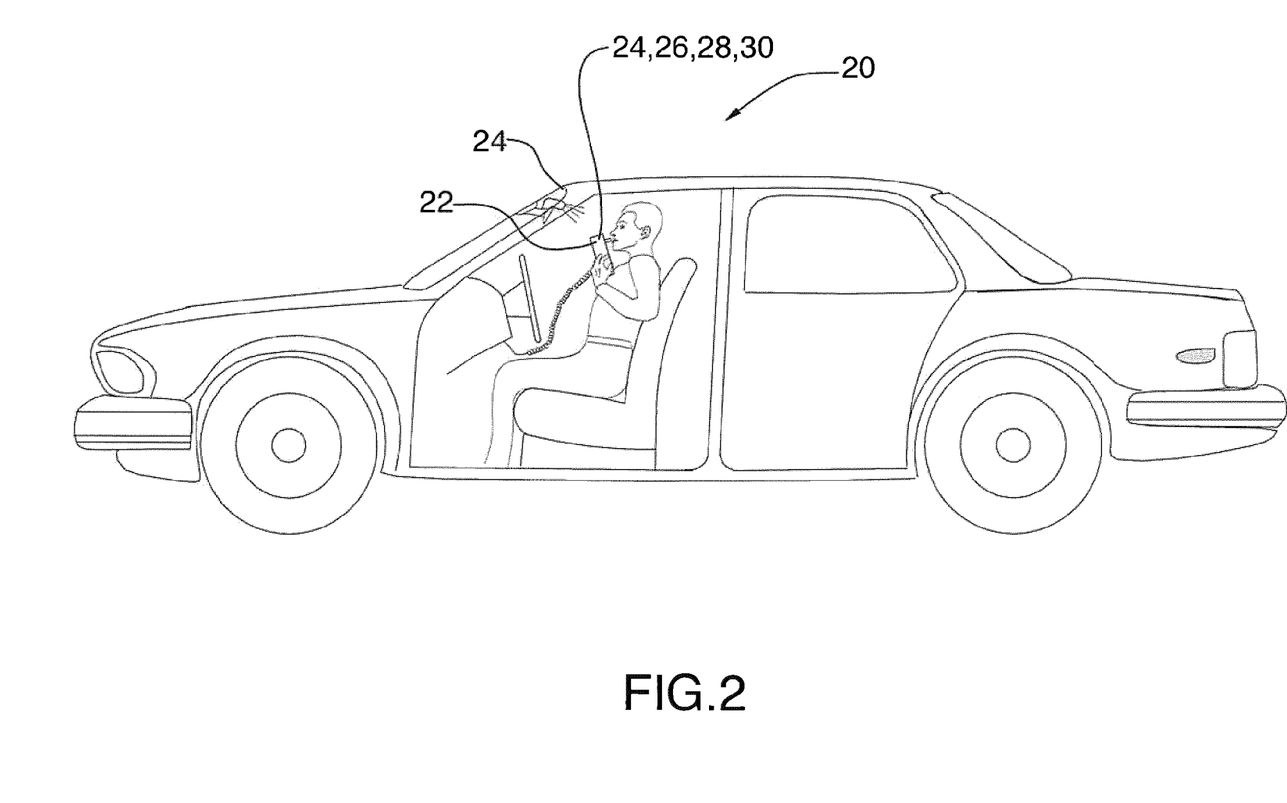
FIG. 2 is a view similar to FIG. 1 showing a system according to an exemplary embodiment of the invention.

As shown in FIG. 2, the exemplary system 20 includes, in addition to a handpiece 22 and an infrared camera 24 as suggested above, a sensor arrangement 26, a light 28 which can be perceived by the imaging device and a computing functionality 30.

The sensor arrangement 26 includes a gyroscope and an accelerometer disposed interiorly of the handpiece 22 and adapted to provide information from which an orientation and location of the handpiece 22 can be calculated. The use of gyroscopes and accelerometers to accommodate these goals is a matter of routine to persons of ordinary skill in the art and accordingly further detail is neither required nor provided.

The light 28, which is an infrared light, is mounted on the handpiece 22 and is selectively triggered by the system 20 according to a pattern which may be or appears random.

The computing functionality 30 carries out a plurality of functions.

Figure 3A:
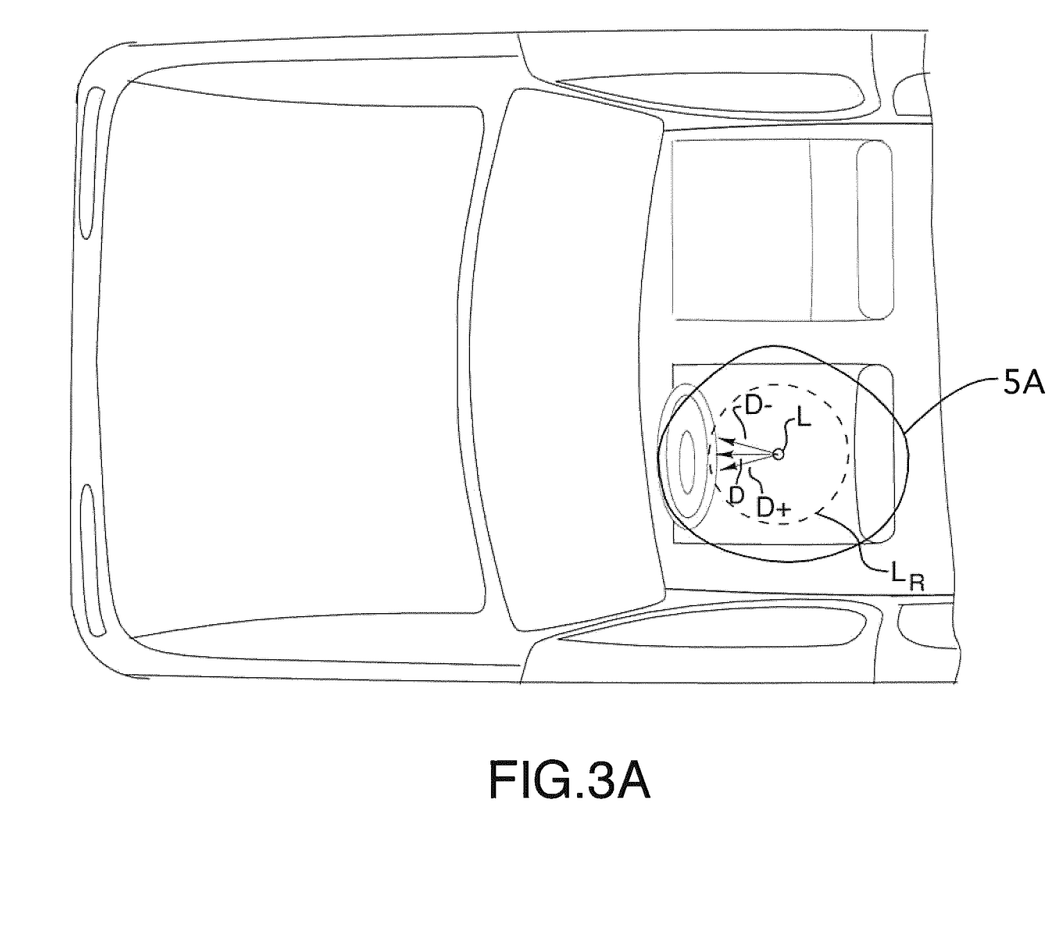
FIG. 3A is a top schematic view of a vehicle showing the calculated location and orientation of a handpiece, and associated error margins.
Figure 3B:
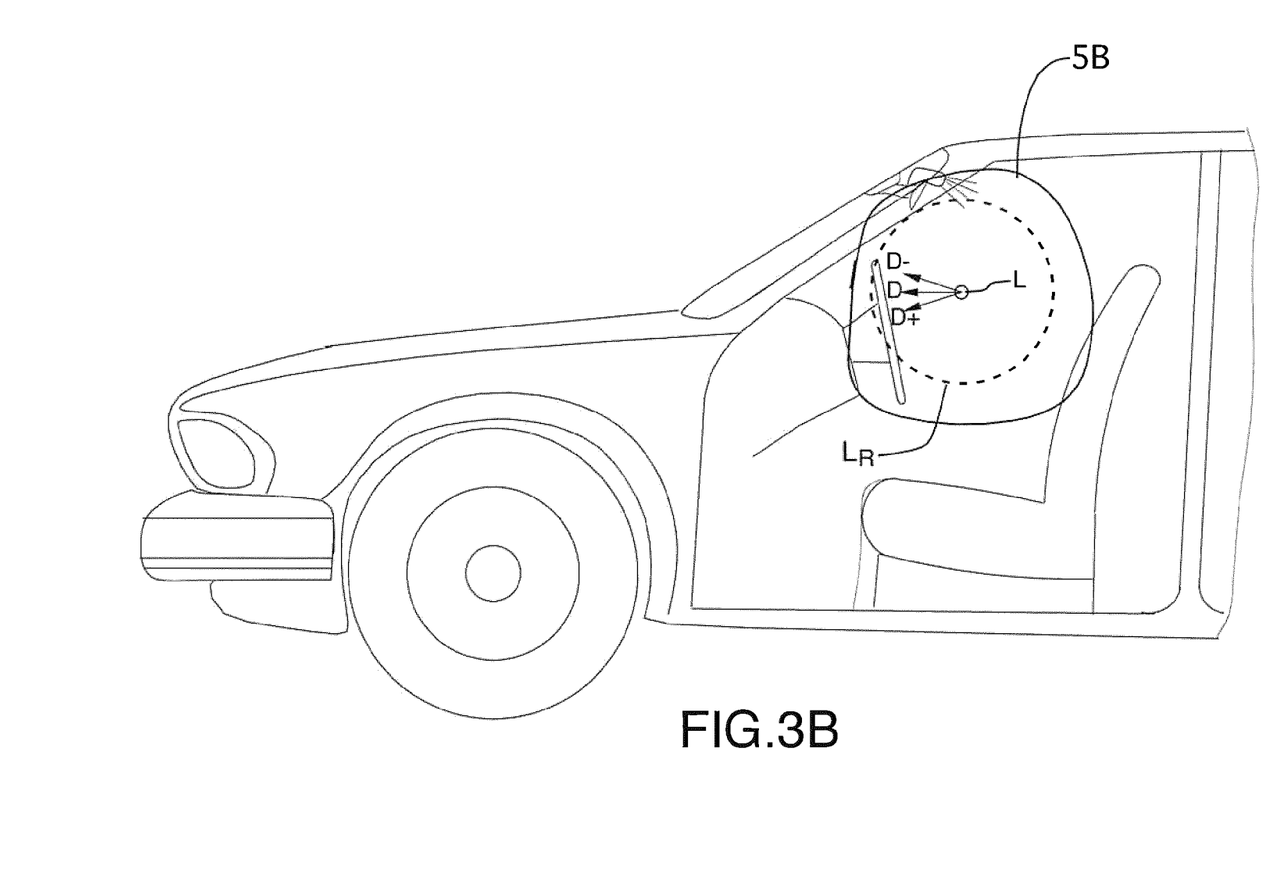
FIG. 3B is a side schematic view of the structure of FIG. 3A.
Figure 4A:
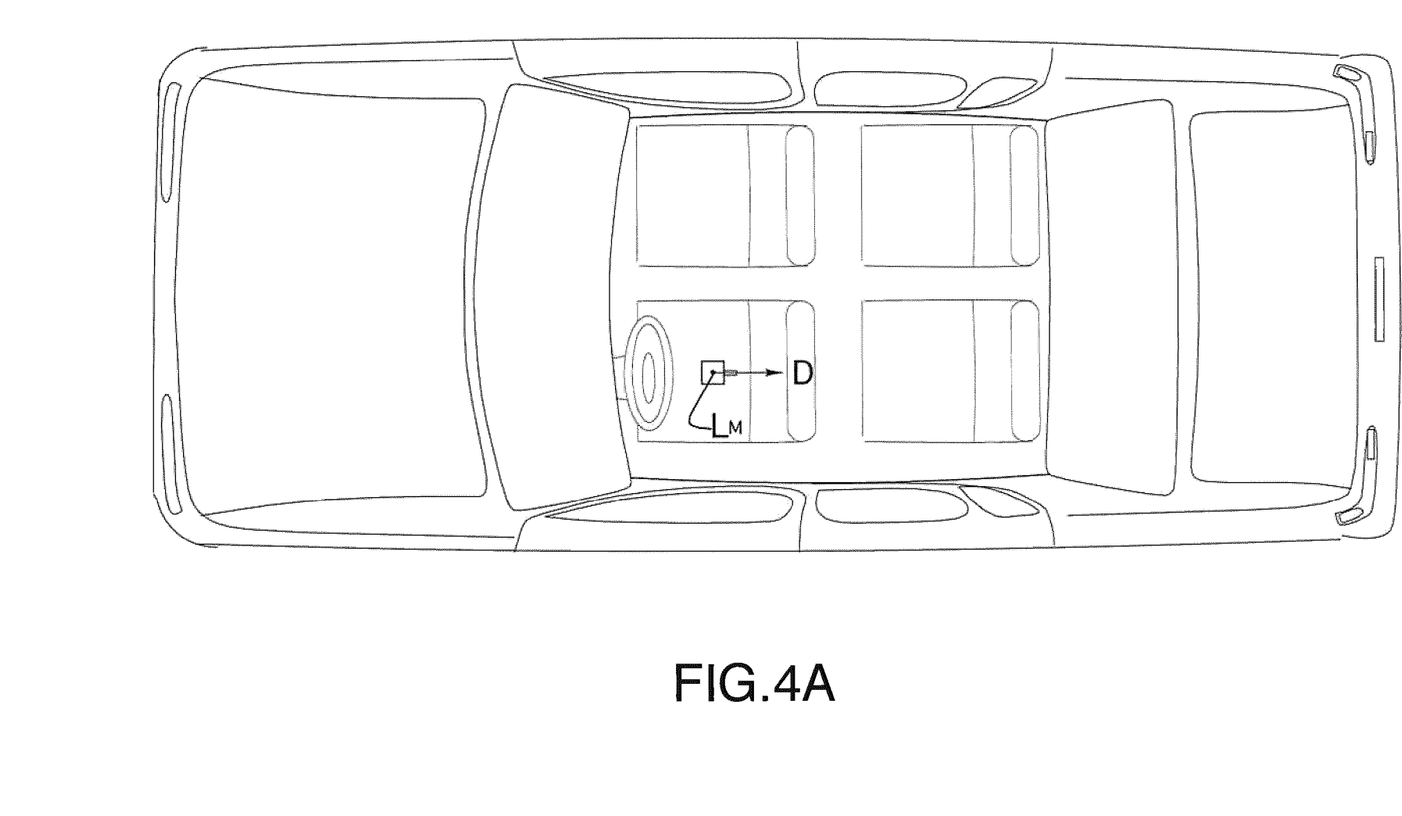
FIG. 4A is a top schematic view of a vehicle showing the actual location and orientation of a handpiece.
Figure 4B:
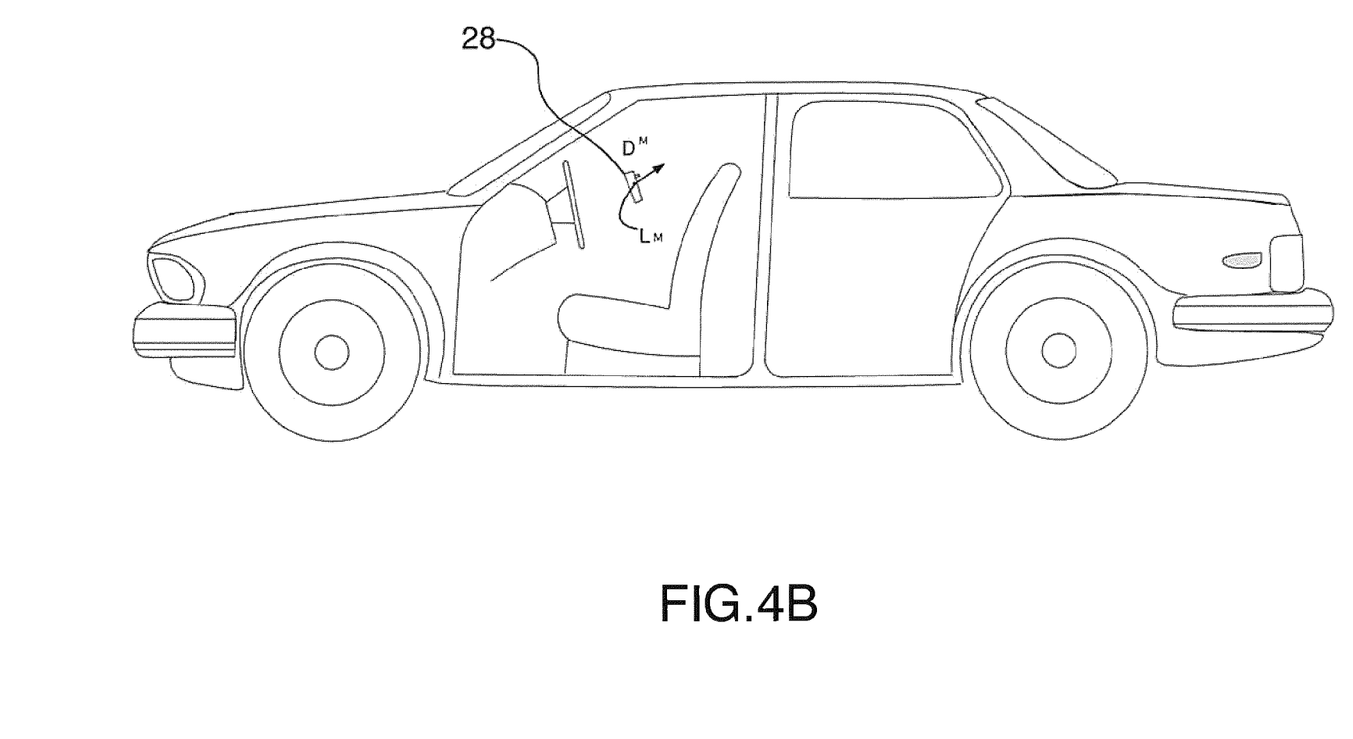
FIG. 4B is a side schematic view of the structure of FIG. 4A.

One such function is the generation of a calculated orientation and position of the handpiece, based upon information obtained from the sensor arrangement 26. This is shown graphically in FIGS. 3A and 3B by the vector D and location L. The calculated orientation and position, being derived from the sensor arrangement, which has a known level of uncertainty, have their own associated uncertainty; this is indicated by the flanking vectors $D^+$ and $D^-$ as well as the encircled area $L^R$ Another such function is the precise location, when present, of the handpiece in the image captured by the imaging device 24 and the production of a measured orientation and position, this being illustrated graphically in FIGS. 4A and 4B by vector $D^M$ and location $L^M$. The location of a handpiece in an image using, for example, edge detection algorithms, is a matter of routine to persons of ordinary skill in the art, and accordingly, further detail is neither required nor provided. In the exemplary embodiment, the location step is done, or perhaps, better stated, is facilitated, using the calculated orientation and location of the handpiece and stored data associated with the shape of the handpiece. That is, the calculated orientation and location and stored data is used by the computing functionality to focus the various searches and decisions associated with the location step, to obtain the desired orientation and position information with a relatively good combination of precision, performance and cost.

Figure 5A:
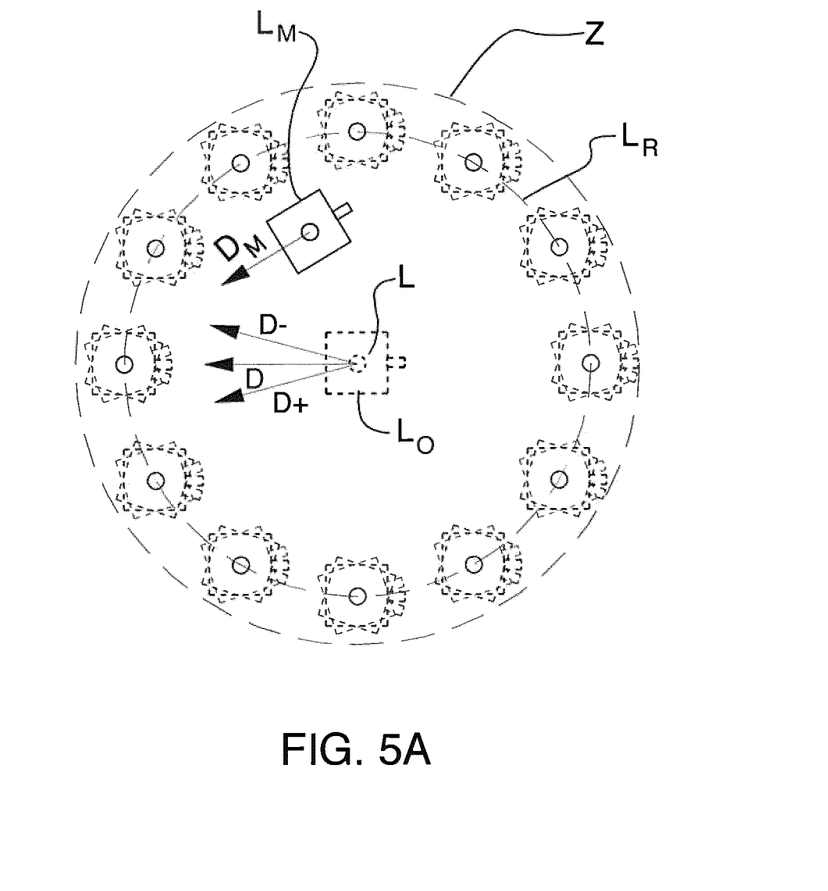
FIG. 5A is an enlarged view of encircled area 5A of FIG. 3A.
Figure 5B:
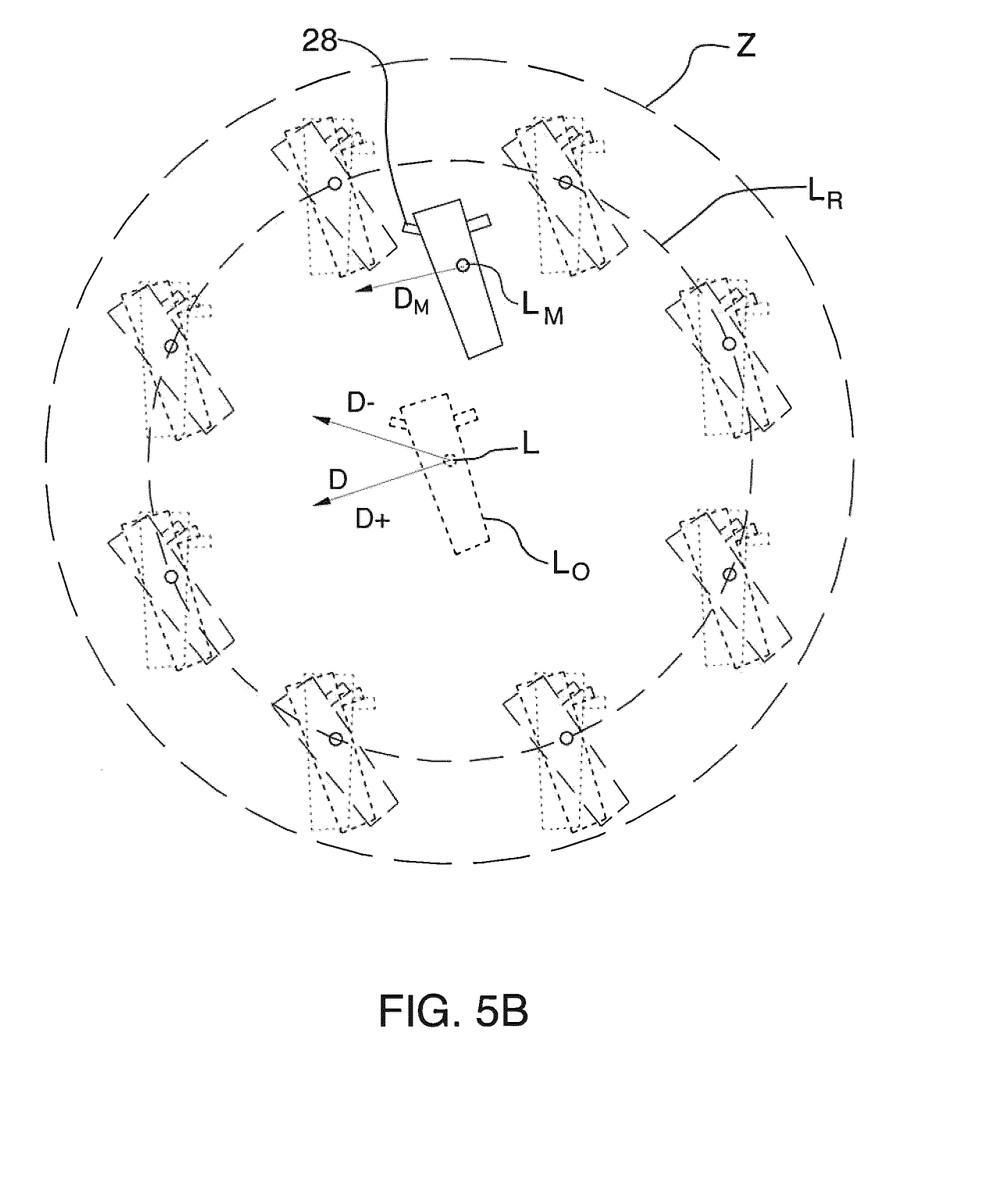
FIG. 5B is an enlarged view of encircled area 5B of FIG. 3B.

For clarification in this regard, reference is made to FIGS. 5A and 5B, which show the various locations of the handpiece associated with the range of locations associated with the error ranges. In both drawings: $L^0$ shows the location and orientation of the handpiece as calculated from location L and vector D; zone Z shows the totality of the space potentially occupied by the handpiece in consideration of uncertainties $D^-$, $D^+$ and $L^R$; and $L^M$ and $D^M$ show the location and direction of the handpiece as actually located through measurement. For greater certainty, it will be understood that, as one way to expedite the step of locating the handpiece in the image, all areas in the image outside zone Z can be ignored. Persons of ordinary skill in the art will recognize that the above is merely an example, and the actual methodology by which the expected location of the handpiece will be used to facilitate the analysis of the image will depend upon the methodologies used and the visual features of the handpiece. For example, only, if the handpiece has features that are easily identified, a methodology may be employed wherein the system looks for these features within subsets of zone Z. Alternatively, if the error ranges are relatively small, and the handpiece is relatively featureless and is most easily identified by overall shape, then the computing functionality will focus the analysis towards the internal perimeter of zone Z and looks for edges that could be the edge of the handpiece.

Another such function is the precise location, when a face is present in the image, of the features thereof. Again, face detection in an image is a matter of routine to persons of ordinary skill in the art and accordingly, details are neither provided nor required. In the exemplary embodiment, this is done using (i) the calculated orientation and location of the handpiece or the measured orientation and position of the handpiece; and (ii) stored data associated with the face of the person. That is, the calculated orientation and location and stored data is used by the computing functionality to focus the various searches and decisions associated with the location step, to obtain the desired location information with a relatively good combination of precision, performance and cost.

Figure 6:
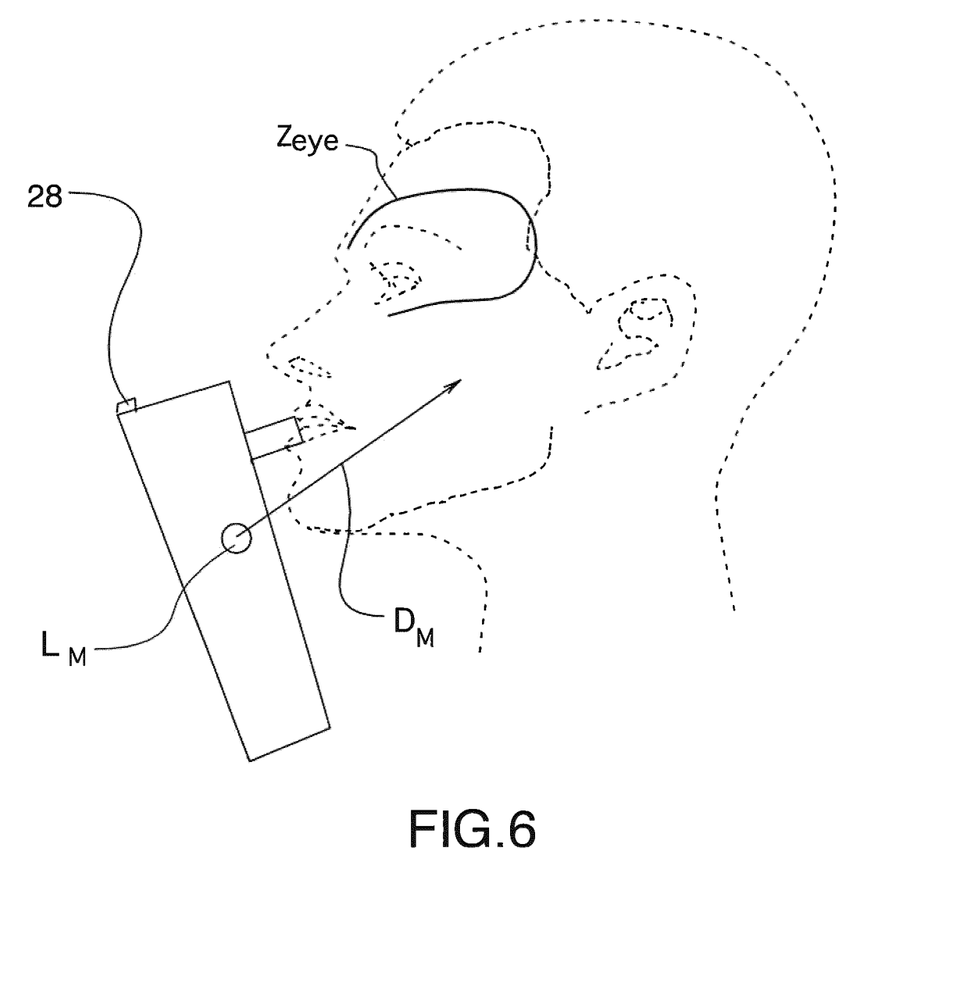
FIG. 6 is a side view of a handpiece showing an image of a face of a user of the handpiece showing probable locations of the eyes of the face of a person delivering a sample to a handpiece.

For clarification and explanation, reference is made to FIG. 6. Herein, location $L^M$ and vector $D^M$ show the location and orientation of the handpiece, as identified by the imaging device and zones $Z^{eye}$ show areas in which the eyes of the contributor of the sample would be expected to appear, based upon previously measured geometric structures associated with the head of the contributor. In this regard, it will be understood that, in FIG. 6, the dotted outline shows the expected location of the head of the user, given the location $L_M$ and orientation $D_M$ of the handpiece. In the exemplary embodiment, it is in these zones that the computing functionality focuses its searches the image for indicia of the eyes of the contributor, to identify the face of the contributor in the image. In the exemplary embodiment, the zones are defined as structures located and orientated at the expected position of the feature, based upon the stored geometric data, but are arbitrarily sized as a multiple of two of the feature being sought, to allow for changes in the face of the user and personal choice in terms of the manner in which the handpiece is held.

Figure 7:
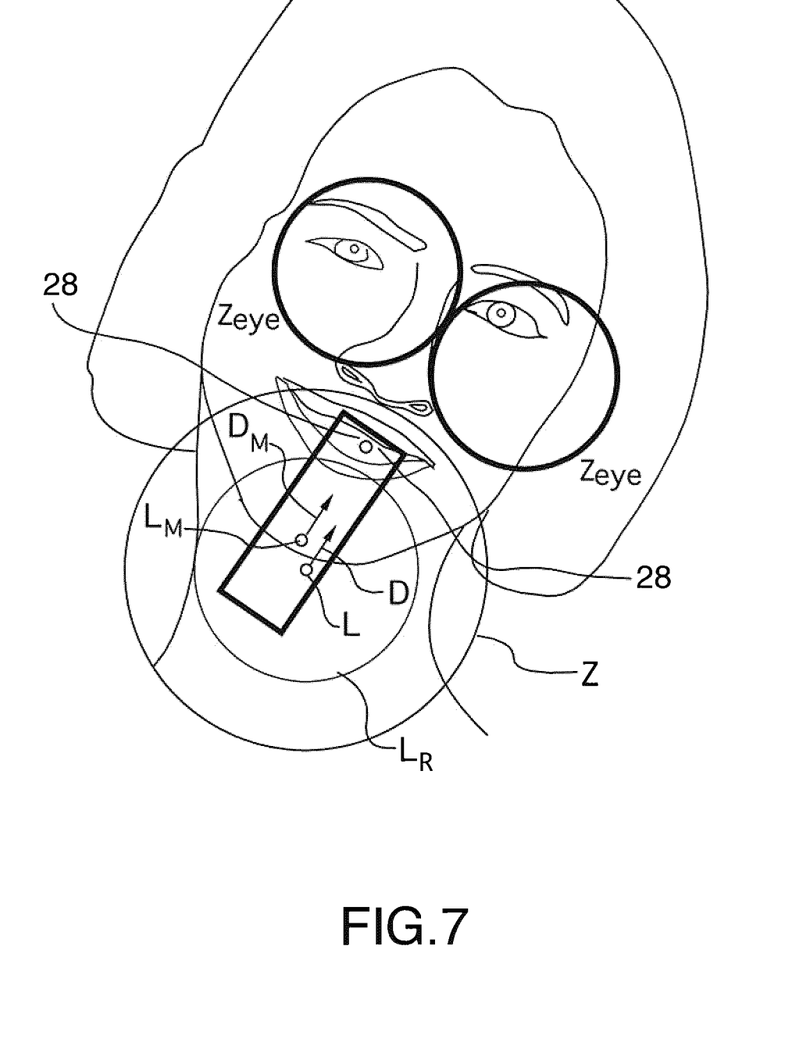
FIG. 7 is an image of a face of a user of the handpiece showing probable locations of the eyes of the face of a person delivering a sample to a handpiece.

Reference is also made to FIG. 7, which demonstrates the functionality at work. The image shows the face of a user of the handpiece, as viewed from the camera. L and D show the position and direction of the handpiece, as calculated from the internal sensors. Z shows the zone in which the search for the handpiece was conducted. $L_M$ and $D_M$ show the actual location and direction of the handpiece, as identified by the imaging device. Zeye shows the zones in which the search for the eyes of the user are carried out, based upon the stored geometric information of the face of the user.

Another such function is the calculation of an expected location of the facial features of the contributor, based upon the measured orientation and position of the handpiece and stored data associated with facial features of the person. This, of course, is effectively a subset of the methodology indicated above and as such is not described further.

Another such function is the calculation of an expected location of the light 28 based upon stored data associated with the shape of the handpiece and further based upon the calculated orientation and location of the handpiece or the measured orientation and position of the handpiece. Again, given that the location of the light is fixed relative to the handpiece, it is a matter of routine to predict a location of the light when the location and orientation of the handpiece are available.

Another such function is identification of the light, using the calculated location of the light. That is, the calculated location of the light is used by the computing functionality to focus the search for the light in the image, which enables the identification of the pattern with a relatively good combination of precision, performance and cost.

A further such function is a verification step, wherein:

the calculated orientation and position of the handpiece is compared to the measured orientation and position the located facial features of the contributor are compared against stored data associated with facial features of the person the pattern sensed is compared against the pattern produced by the system the expected location of the light is compared to the measured location of the light It will be appreciated that each of the foregoing provides information of advantage in the context of offender programs. If the calculated orientation and position of the handpiece differs widely from that measured, this would be evidence that a dummy handset was being used or that the device was not operating property.

If the located facial features of the contributor closely match, in terms of geometrical relation, the stored data of the offender, this would provide evidence, if the breath sample showed alcohol consumption, that the offender had been drinking, which could invite prosecution.

If the sensed light does not match the pattern, this would again be evidence of spoofing or malfunction.

Similarly, if the expected location of the light differed widely from the measured location, this could be evident that the handpiece had been tampered with.

In either event, this could trigger a demand by the provider of the system to return the unit for inspection, so as to ensure that the operator is not inconvenienced by malfunction and the public is not put at risk by tampering.

Whereas a specific embodiment is herein described, it will be evident that variations are possible.

For example, whereas infrared rights and sensors are mentioned, this is not necessary. Simple optical cameras could, for example, be used.

Whereas a gyroscope and an accelerometer are expressly mentioned as forming the basis of the locating too, this is not required. Other methodologies can be used for the purpose of identifying the location of the handpiece and in this regard, the disclosure of U.S. patent application Ser. No. 13/526,202 is incorporated herein by reference.

As well, whereas image analysis tools such as edge detection are mentioned, other methodologies for image recognition can and will be used by persons of ordinary skill in the art.

Further, whereas the exemplary embodiment contemplates the use of a measured location of the handpiece, in combination with stored geometrical relations of the face of the user, to focus the search results, this is not necessary. Without intending to be bound by theory, it is believed that the handpiece, being fixed in shape, can be relatively quickly and accurately identified in an image using conventional analysis tools, which, when overlaid with stored geometry of the face of the user, will enable the relatively more difficult to identify features of a face to be relatively quickly found. However, much of the advantage of the invention could potentially be obtained simply by overlying stored geometric relations of, for example, an average person onto the calculated location and orientation of the handpiece.

Finally, but without limitation, whereas a pattern of light is contemplated to be used for anti-circumvention purposes, this could be omitted.

Accordingly, the invention should be understood as limited only by the accompanying claims, purposively construed.

The invention claimed is:

1. An improved breath alcohol ignition interlock system of the type for use by a person and including a handpiece and an imaging device, the handpiece containing a breath alcohol tester and the imaging device being adapted to capture an image including the handpiece when a breath sample is delivered to the handpiece, the improvement comprising:
   a sensor arrangement adapted to provide information from which an orientation and position of the handpiece can be calculated;
   a computing functionality adapted to: generate a calculated orientation and position of the handpiece; and if a face appears in the image, precisely locate the features thereof
   wherein the features of the face are located using the calculated orientation and position of the handpiece.

2. The system according to claim 1, wherein the features of the face are further located using stored data associated with facial geometry.

3. The system according to claim 2, wherein the features of the face are further located using stored data associated with the geometry of the face of the person.

4. The system according to claim 3, wherein
   if the handpiece appears in the image, precisely identify the location and orientation of the handpiece, using stored data associated with the geometry of the handpiece.

5. The system according to claim 3, wherein
   the handpiece includes a light which is selectively triggered by the system according to a pattern and can be perceived by the imaging device; and
   the imaging device senses the light and compares the perceived light against the pattern for anti-circumvention purposes.

6. The system according to claim 2, wherein
   if the handpiece appears in the image, precisely identify the location and orientation of the handpiece, using stored data associated with the geometry of the handpiece.

7. The system according to claim 6, wherein the features of the face are located using the location and orientation of the handpiece as identified.

8. The system according to claim 7, wherein
   the handpiece includes a light which is selectively triggered by the system according to a pattern and can be perceived by the imaging device; and
   the imaging device senses the light and compares the perceived light against the pattern for anti-circumvention purposes.

9. The system according to claim 6, wherein
   the handpiece includes a light which is selectively triggered by the system according to a pattern and can be perceived by the imaging device; and
   the imaging device senses the light and compares the perceived light against the pattern for anti-circumvention purposes.

10. The system according to claim 2, wherein
    the handpiece includes a light which is selectively triggered by the system according to a pattern and can be perceived by the imaging device; and
    the imaging device senses the light and compares the perceived light against the pattern for anti-circumvention purposes.

11. The system according to claim 1, wherein the sensor arrangement comprises an accelerometer and a gyroscope disposed interiorly of the handpiece.

12. The system according to claim 11, wherein
    the handpiece includes a light which is selectively triggered by the system according to a pattern and can be perceived by the imaging device; and the imaging device senses the light and compares the perceived light against the pattern for anti-circumvention purposes.

13. The system according to claim 1, wherein
the handpiece includes a light which is selectively triggered by the system according to a pattern and can be perceived by the imaging device; and
the imaging device senses the light and compares the perceived light against the pattern for anti-circumvention purposes.

14. The system according to claim 13, wherein the computing functionality senses the light using
stored data associated with the shape of the handpiece and the location of the light therein
and
the calculated orientation and location of the handpiece or the measured orientation and location of the handpiece.

* * * * *